US007658767B2

(12) United States Patent
Wyss

(10) Patent No.: US 7,658,767 B2
(45) Date of Patent: Feb. 9, 2010

(54) HINGED ORTHOPAEDIC PROSTHESIS

(75) Inventor: Joseph G. Wyss, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 253 days.

(21) Appl. No.: 11/428,066

(22) Filed: Jun. 30, 2006

(65) Prior Publication Data

US 2008/0004708 A1   Jan. 3, 2008

(51) Int. Cl.
    *A61F 2/38* (2006.01)
(52) U.S. Cl. .................................. 623/20.29
(58) Field of Classification Search ............. 623/20.24, 623/20.28, 20.29
    See application file for complete search history.

(56) References Cited

U.S. PATENT DOCUMENTS

| 4,064,568 | A | * | 12/1977 | Grundei et al. | .......... 623/20.26 |
| 4,219,893 | A | | 9/1980 | Noiles | |
| 4,262,368 | A | | 4/1981 | Lacey | |
| 4,301,553 | A | * | 11/1981 | Noiles | ..................... 623/20.25 |
| 4,470,158 | A | | 9/1984 | Pappas et al. | |
| 4,865,606 | A | * | 9/1989 | Rehder | ..................... 623/20.23 |
| 5,800,552 | A | * | 9/1998 | Forte | ....................... 623/20.27 |
| 5,824,096 | A | | 10/1998 | Pappas et al. | |
| 6,099,570 | A | * | 8/2000 | Livet et al. | ............... 623/20.21 |
| 6,485,519 | B2 | | 11/2002 | Meyers et al. | |
| 2004/0249467 | A1 | * | 12/2004 | Meyers et al. | ............ 623/20.24 |
| 2005/0192672 | A1 | | 9/2005 | Wyss et al. | |

FOREIGN PATENT DOCUMENTS

| DE | 3343606 | 7/1985 |
| FR | 2760352 | 9/1998 |
| FR | 2776919 | 10/1999 |

OTHER PUBLICATIONS

European Search Report for European Patent Application No. 07252632.0-2310, Oct. 19, 2007, 8 pgs.

* cited by examiner

*Primary Examiner*—Thomas J Sweet
(74) *Attorney, Agent, or Firm*—Barnes & Thornburg LLP

(57) ABSTRACT

A hinged orthopaedic knee prosthesis includes a femoral component, a tibial component, and a bearing component positioned between the femoral and tibial components. A hinge assembly is coupled to the femoral component to constrain the movement of the femoral component relative to the tibial component.

21 Claims, 8 Drawing Sheets

HINGED ORTHOPAEDIC PROSTHESIS

FIELD OF THE DISCLOSURE

The present disclosure relates generally to an orthopaedic prosthesis, and more particularly to a knee prosthesis. Specifically, the present disclosure relates to a hinged orthopaedic prosthesis.

BACKGROUND

Movement (e.g., flexion and extension) of the natural human knee involves movements of the femur and the tibia. Specifically, during flexion and extension, the distal end of the femur and the proximal end of the tibia articulate relative to one another through a series of complex movements. Damage (e.g., trauma) or disease can deteriorate the bones, articular cartilage, and ligaments of the knee, which can ultimately affect the ability of the natural knee to function in such a manner. As a result, knee prostheses have been developed and implanted into surgically prepared ends of the femur and tibia.

A typical knee prosthesis for a total knee replacement, for example, includes a tibial component or tibial tray coupled to the patient's tibia, a femoral component coupled to the patient's femur, and a bearing component positioned between the tibial tray and the femoral component and including a bearing surface to accommodate the condyles of the femoral component. A constrained knee prosthesis, however, may be used when a patient's collateral ligaments have been damaged or are otherwise not able to provide adequate support and stability to the knee. One such constrained knee prosthesis is a hinged knee prosthesis which typically includes a hinge mechanism to couple the femoral component to one or both of the bearing component and the tibial components in order to constrain and mechanically link the components of the knee prosthesis together. As such, hinged knee prostheses typically operate to transfer much of the joint load from the femur to the tibia through the hinge. Alternatively, the bearing may operate to transfer applied loads from the femoral component to the tibial component. By reducing or eliminating the need of the hinge mechanism to support load transfer, the hinge mechanism may be directed primarily toward providing stability.

SUMMARY

The present invention comprises one or more of the features recited in the appended claims or the following features or combinations thereof:

According to one aspect of the present disclosure, a hinged knee prosthesis includes a femoral component configured to be coupled to a femur and including a body having an elongated slot formed therein, a tibial component configured to be coupled to a tibia and defining a cavity, and a bearing component positioned between the femoral component and the tibial component. A hinge assembly of the knee prosthesis includes a piston and a hinge pin. The hinge pin is configured to be received within the cavity of the tibial component and the hinge pin is received through both a bore formed in the piston and the elongated slot of the femoral component.

Illustratively, the bearing component includes an aperture and the piston is received through the aperture of the bearing component. Further illustratively, the elongated slot may be formed in a first side wall of the femoral component while a second elongated slot may be formed in a second side wall of the femoral component. The first and second side walls are spaced-apart from each other and the hinge pin may be received through each of the first and second elongated slots. Further still, the piston may include a head and a shaft coupled to the head such that the bore of the piston is formed through the head of the piston and the head of the piston is positioned between the first and second side walls of the femoral component.

Illustratively, the hinge pin, the femoral component, and the piston may each be made from metal while the bearing component may be made from a polymer. A polymer bearing of the hinge assembly may be coupled to the pin and positioned between the pin and the portion or side wall of the femoral component defining the slot.

A slot cover may be provided to be coupled to the femoral component in order to cover the elongated slot.

Illustratively, the elongated slot may be generally straight or may be curved. The posterior end of the elongated slot may be positioned superiorly from the anterior end of the elongated slot.

According to another aspect of the present disclosure, a hinged knee prosthesis includes a femoral configured to be coupled to a femur and including an elongated slot formed therein, a tibial component configured to be coupled to a tibia, and a bearing component positioned between the femoral component and the tibial component. A hinge assembly of the prosthesis includes a hinge pin received through the elongated slot of the femoral component.

Illustratively, the elongated slot may be curved. As such, the curvature of the elongated slot may follow the curvature of a condylar member of the femoral component. Alternatively, the elongated slot may be generally straight.

Further illustratively, the hinge assembly may include a piston having a bore formed therein such that the hinge pin is received through the bore. The piston may include a head defining the bore and a stem coupled to the head and received within an elongated cavity of the tibial component. The piston may be received through an aperture formed in the bearing component.

Alternatively, the bearing component may include a spine positioned between a medial bearing surface and a lateral bearing surface of the bearing. As such, the hinge pin may be received through a bore formed in the spine. Further illustratively, the femoral component may include a first side wall formed to define the elongated slot and a second side wall formed to define a second elongated slot such that the spine of the bearing component is positioned between the first and second side walls of the femoral component. The femoral component and the bearing component may be configured to rotate together relative to the tibial component about an axis through a stem of the tibial component.

According to yet another aspect of the present disclosure, a hinged prosthetic joint for accommodating articulation between a first bone and a second bone includes a first component configured to be attached to the first bone and a second component configured to be attached to the second bone. The first component includes a body formed to define an elongated slot. A bearing component of the joint is positioned between the first and second components and a hinge assembly of the joint includes a hinge pin received within the slot of the first component.

The above and other features of the present disclosure will become apparent to those skilled in the art upon consideration of the following detailed description and accompanying drawings of illustrative embodiments exemplifying the best mode of carrying out the disclosure as presently perceived.

BRIEF DESCRIPTION OF THE DRAWINGS

The detailed description particularly refers to the accompanying figures in which.

DETAILED DESCRIPTION OF THE DRAWINGS

Figure 1:
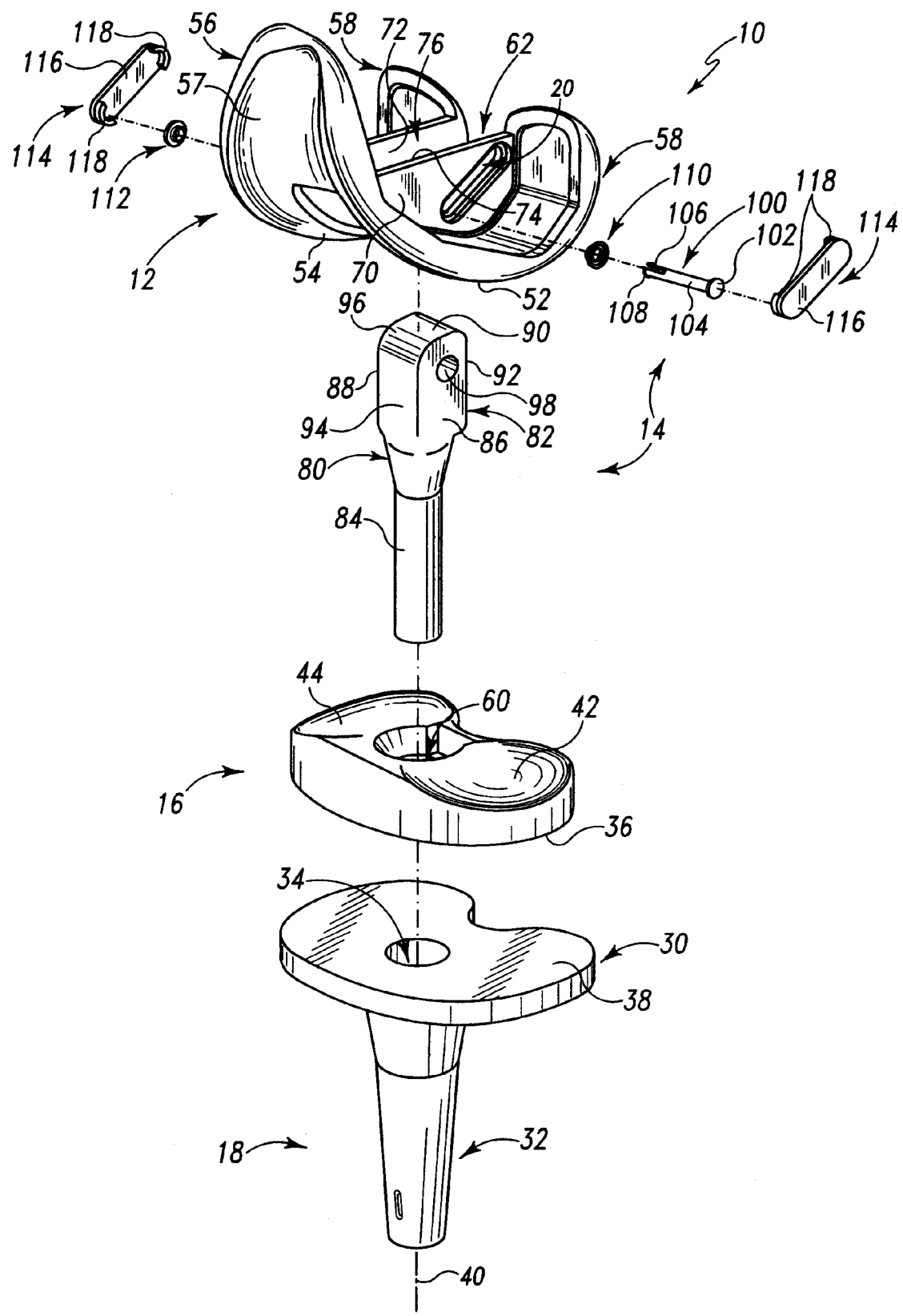
FIG. 1 is an exploded, perspective view of a hinged knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Figure 2:
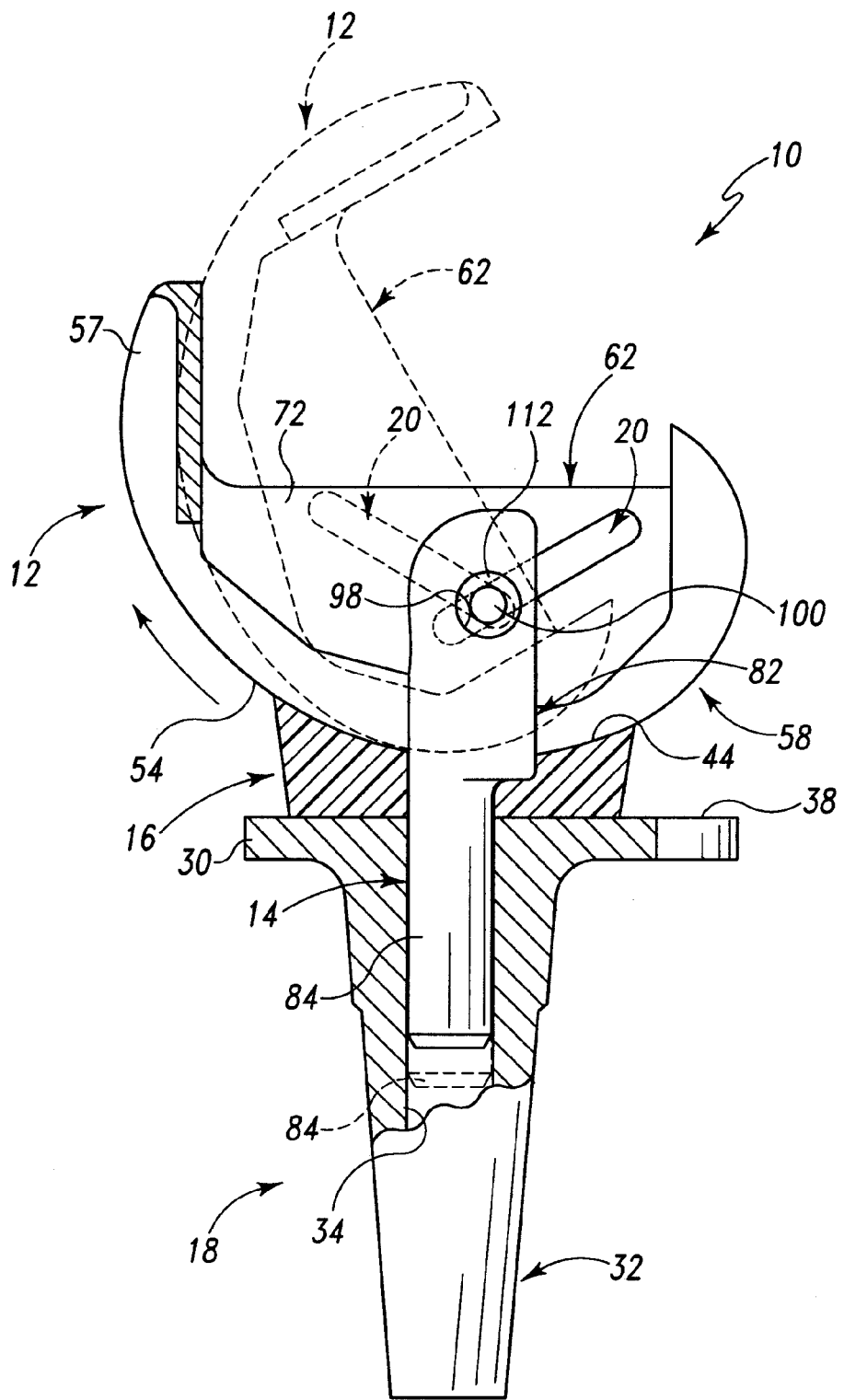
FIG. 2 is a part-sectional side view of the hinged knee prosthesis of FIG. 1 showing, in phantom, motion of a femoral component of the hinged knee prosthesis.

Looking to FIGS. 1 and 2, a hinged prosthetic device, illustratively, a hinged knee prosthesis 10, includes a femoral component 12, a hinge assembly 14, a bearing component 16, and a tibial component or tray 18. As is discussed in greater detail below, the hinge assembly 14 is pivotably coupled to the femoral component 12 and is received within the tibial tray 18 in order to stabilize relative movement between the femoral component 12 and the bearing component 16. Further, the hinge assembly 14 is received through elongated guide slots 20 of the femoral component 12 in order to guide the movement of the femoral component 12 relative to both the bearing component 16 and the tibial component 18. Such movement of the femoral component 12 as guided by the slots 20 and the hinge assembly 14 provides for a more even distribution of weight loads from the femoral component 12 across the bearing component 16 and to the tibial tray 18 during movement of the knee prosthesis 10 between flexed and extended positions.

Looking still to FIGS. 1 and 2, the tibial tray 18 includes a platform 30 from which a stem 32 extends. The tibial stem 32 is configured to be implanted into a prepared end of a patient's tibia (not shown). An elongated cylindrical cavity 34 of the tibial tray 18 is formed through the platform 30 and within the stem 32 of the tibial tray 18. The illustrative bearing component 16 includes a generally flat bottom surface 36 configured to rest upon the generally flat top surface 38 of the platform 30. Illustratively, the bearing component 16 is rotatable relative to the tibial tray 18 about an axis 40 running through the elongated cylindrical cavity 34 of the tibial tray 18.

The bearing component 16 further includes a lateral bearing surface 42 and a medial bearing surface 44. The bearing surfaces 42, 44 are configured to articulate with a lateral condyle surface 52 and a medial condyle surface 54, respectively, of the femoral component 12, as discussed below. The bearing component 16 further defines an aperture or slot 60 extending through the body of the bearing component 16. Illustratively, the slot 60 is positioned between the bearing surfaces 42, 44 of the bearing component 16 and is configured to be aligned with the cylindrical cavity 34 of the tibial tray 18. The slot 60 slidably receives a portion of the hinge assembly 14 therethrough, as is discussed in greater detail below. Illustratively, the hinge assembly 14 and the slot 60 are shaped to prevent axial rotation of the hinge assembly 14 relative to the bearing component 16 about the axis 40 shown in FIG. 1. As such, the hinge assembly 14 and the bearing component 16 rotate together relative to the tibial tray 18 about the axis 40. As is further discussed below, the hinge assembly 14 is coupled to the femoral component 12 such that the femoral component 12 is also able to rotate with the hinge assembly 14 and the bearing component 16 about the axis 40.

Figure 9:
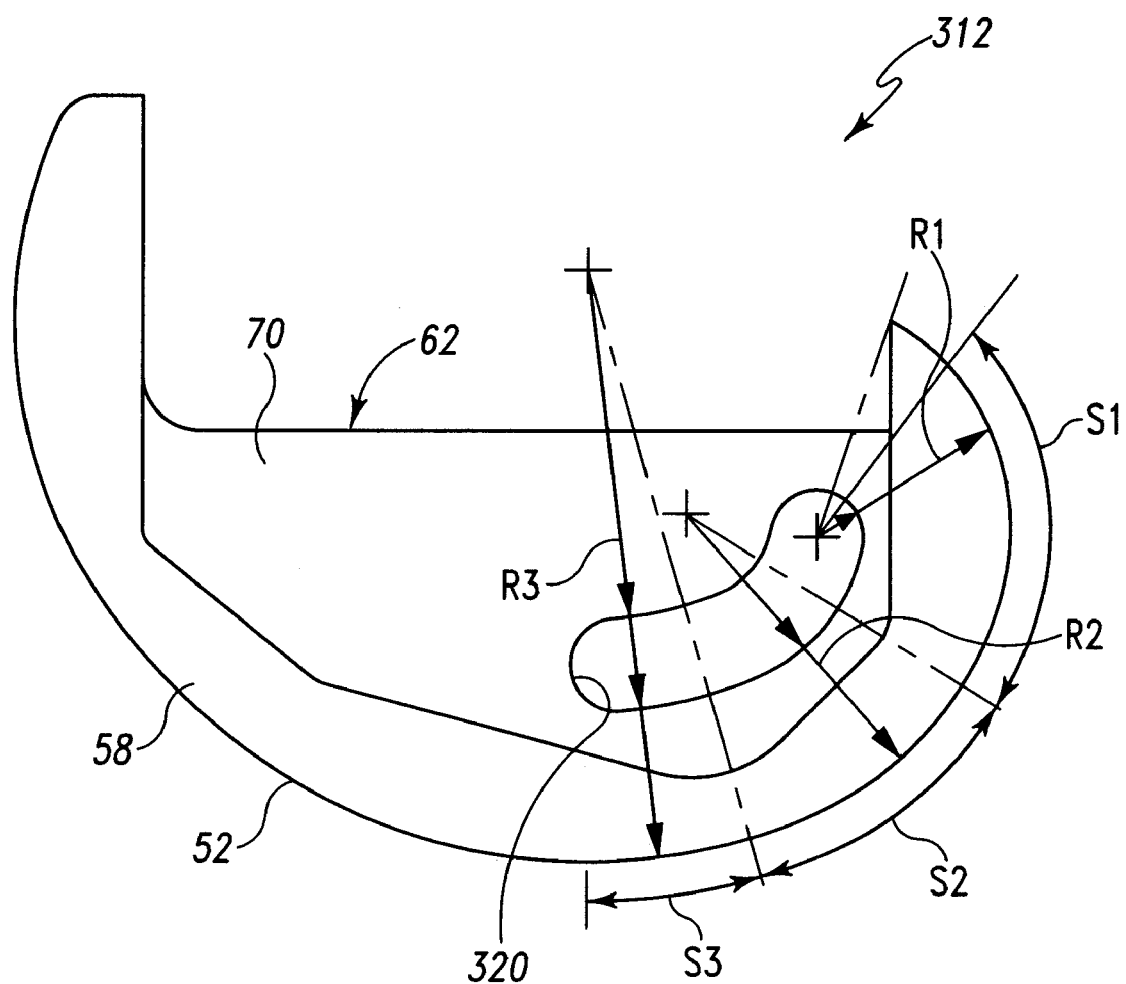
FIG. 9 is a diagrammatic view of a femoral component having a slot formed within a side wall of the femoral component which follows the curvature of an outer condylar surface of the femoral component.

The femoral component 12 is configured to be implanted into a prepared end of the patient's femur (not shown), and is configured to emulate the configuration of the patient's natural femoral condyles (not shown). As such, the femoral component 12 includes a body 56 having a pair of spaced-apart lateral and medial condylar members 58 which each include the respective lateral condyle surface 52 and the medial condyle surface 54 formed to articulate with the bearing 16. These outer, curved surfaces 52, 54 each include curved segments S1, S2, and S3 each having a radii R1, R2, and R3 respectively, as shown diagrammatically with reference to a similar femoral component 312 in FIG. 9, for example. The segments form a smooth surface in which the radii at the interface between the adjacent surface segments having common tangents. As such, the lateral condyle surface 52 and the medial condyle surface 54 are configured (e.g., curved) in a manner which mimics the condyles of a natural femur. An anterior patellar flange 57 of the femoral component 12 is integral with and interconnects anterior portions of the condyle members 58.

A cam box 62 of the femoral component 12 is positioned between and coupled to the condylar members 58. Illustratively, the cam box 62 includes first (or lateral) and second (or medial) side walls 70, 72 which are coupled to and project from the body 56 of the femoral component 12. Illustratively, each of the first and second side walls 70, 72 is formed integrally with the corresponding lateral and medial condylar member 58. Each side wall 70, 72 defines a top wall 74 of the cam box 62 and an opening 76 of the cam box 62 is provided between the side walls 70, 72.

As shown in FIGS. 1 and 2, the elongated slot or track 20 is formed in each side wall 70, 72. Illustratively, each elongated slot 20 is angled to define an imaginary line extending from an anterior/inferior front end of each slot 20 toward a posterior/superior back end of each slot 20. In other words, the longitudinal axis of each slot 20 is each angled upwardly such that a posterior end of each slot 20 is positioned higher than an anterior end of each slot 20. Further, the slots 20 of the femoral component 12 are generally straight, rather than curved, for example. However, it is within the scope of this disclosure for the slots 20 to be curved as well. Further, while the slots 20 are shown to have a particular length and width relative to other features of the femoral component 12, it is within the scope of this disclosure to provide a slot having any suitable length and width. As is discussed in greater detail below, a portion of the hinge assembly 14 is coupled to the cam box 62 and slides along the tracks 20 of the cam box 62.

Although not shown, it should be understood that the femoral component 12, as well as other femoral components shown in the figures and discussed herein, each include a rod support (not shown) coupled to the body 56 in a position generally between the condylar members 58. The rod support is formed to receive a stabilizing rod (not shown) for implantation into the prepared femur of a patient undergoing a total knee replacement surgery, for example. As such, each of the femoral components shown and described herein includes such a rod support and/or stabilizing rod in order to couple the femoral component to a patient's femur.

The components of the knee prosthesis 10 that engage the natural bone, such as the femoral component 12 and the tibial tray 18 may be constructed from a biocompatible metal, such as titanium or cobalt chrome alloy for example. The bone engaging surfaces of these components may be textured to facilitate cementing the component to the bone. Such surfaces may also be porous coated to promote bone ingrowth for permanent fixation. Alternatively, the bearing component 16 may be constructed from a material that allows for smooth articulation and rotation between the bearing component 16 and the adjacent femoral and tibial components 12, 18. One such material is ultra high molecular weight polyethylene (UHMWPE). Of course, the bearing 16 may be made from other suitable polymers as well.

The hinge assembly 14 of the prosthesis 10 includes a metal piston 80 having a head 82 and a shaft 84 coupled to the head 82. The head 82 includes two side walls, illustratively, a lateral side wall 86 and a medial side wall 88, a top wall 90, a posterior wall 92, and an anterior wall 94. Illustratively, a curved surface 96 is defined between the anterior wall 94 and the top wall 90. A bore 98 is formed through the head 82 of the piston 80 and extends from the lateral side wall 86 to the medial side wall 88. In other words, the bore 98 extends in a medial/lateral direction through the head 82 of the piston 80 The shaft 84 generally defines a circular cylinder and is received through the aperture 60 of the bearing component 16 and into the elongated cylindrical cavity 34 of the tibial tray 18. The piston 80 may be made from any suitable metal such as titanium or cobalt chrome alloy, for example. Alternatively, the piston 80 may be made from any suitable polymer as well.

The hinge assembly 14 further includes a hinge pin 100 to be received through the bore 98 formed in the head 82 of the piston 80. As shown in FIG. 2, for example, the hinge pin 100 is also received through the first and second slots 20 formed within the side walls 70, 72 of the femoral component 12 in order to couple the piston 80 to the femoral component 12, as is discussed in greater detail below. The illustrative hinge pin 100 includes a head or cap 102 and a body 104 coupled to the cap 102 which generally defines a circular cylinder. Opposite the cap 102, the body 104 of the pin 100 includes a slot 106 formed therein and a foot or outer rim 108 of the pin 100 is coupled to the body 104.

Further illustratively, the hinge pin 100 is metal; however, it is within the scope of this disclosure for the hinge pin 100 to be made from other suitable materials such as polymers, for example. First and second bearings 110, 112 of the hinge assembly 14 are coupled to the outer ends (i.e., the cap 102 and the outer rim 108) of the hinge pin 100. The bearings 110, 112 are made from a polymer and illustratively operate to provide a bearing surface between the metal hinge pin 100 and the metal femoral component 12. In other words, the bearings 110, 112 reduce friction and wear between the hinge pin 100 and side walls 70, 72 of the cam box 62 which define the slots 20 within which the hinge pin 100 translates.

The prosthesis 10 further includes slot covers 114, as shown in FIG. 1, which snap into the slots 20 of the femoral component 12 and shield the slots 20 from the patient's surrounding bone (not shown). Each slot cover 114 includes a generally oval-shaped body 116 and two flanges 118 coupled to opposite ends of each body 116. Illustratively, the flanges 118 are curved or are generally "C-shaped" and are provided to snap into the respective slot 20 in order to couple the slot cover 114 to the femoral component 12. As stated above, the slot covers 114 operate to cover or shield the open slots 20 from the patient's surrounding natural bone in order to help prevent the patient's bone from growing into the slots 20. As such, the slot covers 114 operate to prevent or reduce bone ingrowth into the slots 20.

As stated above, the stem 84 of the piston 80 of the hinge assembly 14 is received through the aperture 60 of the bearing component 16 and into the elongated cylindrical cavity 34 of the tibial tray 18. The head 82 of the piston 80 is positioned within the cam box 62 between the side walls 70, 72 of the femoral component 12 such that the bore 98 of the head 82 is aligned with the slot 20 formed in each side wall 70, 72 of the femoral component 12. The hinge pin 100 is received through the slot 20 formed in the lateral wall 70 of the femoral component 12, the bore 98 of the head 82, and the slot 20 formed in the medial wall 72 of the femoral component 12 in order to couple the piston 80 of the hinge assembly 14 with the femoral component 12. As noted above, the bearings 110, 112 are positioned between the pin 100 and the side walls 70, 72 defining elongated slot or guide track 20.

During movement of the prosthesis 10 between flexed and extended positions, the piston 80 is movable upwardly and downwardly within the cylindrical cavity 34 of the tibial tray 18. Looking to FIG. 2, for example, the hinged knee prosthesis 10 is in the axial position whereby the patient's tibia and femur (not shown) coupled to the tibial tray 18 and the femoral component 12, respectively are extended. In other words, the patient's leg (not shown) is generally straight. In this extended position, the pin 100 of the hinge assembly 14 is generally positioned within the lower, anterior portion of each slot 20 of the femoral component 12. As the hinged knee prosthesis 10 flexes (i.e., the patient's knee bends), the pin 100 of the hinge assembly 14 translates along the slots 20 relative to the femoral component 12. As shown in phantom in FIG. 2, for example, the hinged knee prosthesis 10 is shown in a flexed position such that the piston 80 has moved downwardly relative to the bearing component 16 and the tibial tray 18. Further, the hinge pin 100 of the hinge assembly 14 has translated along the slots 20 formed in the side walls 70, 72 of the femoral component 12 to be positioned at the upper, posterior end of each slot 20.

The piston 80 is able to move up and down as necessary within the cylindrical cavity 34 of the tibial tray 18 as the prosthesis 10 moves between the extended position and various flexed positions. As the prosthesis 10 moves between extended and flexed positions, the elongated slots 20 of the femoral component 12 guide the movement of the femoral component 12 and the hinge assembly 14 relative to the bearing component 16.

As the femoral component 12 flexes and extends, the hinge pin 100 of the hinge assembly 14 is urged to translate along the elongated slots 20 formed in the cam box 62 of the femoral component 12. In turn, the piston 80 of the hinge assembly 14 moves up and down relative to the tibial tray 18 and the bearing component 16 as the femoral component 12 flexes and extends. As discussed above, the slots 20 allow the femoral component 12 to articulate on the bearing component 16 such that the bearing component 16 remains relatively stationary and does not move significantly in the anterior or posterior directions during such articulation. In other words, an axis of rotation of the femoral component 12 is not fixed. Rather, the slots 20 of the femoral component 12 provide a variable axis of rotation of the femoral component 12 about the hinge pin 100 which translates along the slots 20. Such rotational and sliding movement of the femoral component 12 on the bearing component 16 functions to mimic the operation and movement of the patient's natural anatomy. Because the femoral component 12 is able to slide anteriorly and posteriorly on the bearing component 16 to maintain articulating between the condylar surfaces 52, 54 of the femoral component 12 and the bearing surfaces 42, 44 of the bearing component 16, any anterior/posterior movement of the bearing component 16 relative to the tibial tray 18 is reduced. In other words, the bearing component 16 may move slightly anteriorly and posteriorly as the prosthesis 10 is moved between flexed and extended positions. However, reducing the anterior/posterior motion of the bearing component 16 functions to more naturally replicate the operation and motion of a patient's natural anatomy.

Further, such rotational and sliding movement of the femoral component 12 relative to the bearing component 16 about a variable or moving axis of rotation operates to evenly distribute weight loads across the prosthesis 10 as the prosthesis 10 moves between flexed and extended positions. Weight or stress loads are evenly transferred or distributed from the femoral component 12 across the bearing component 16 during the full range of motion or movement of the prosthesis 10 between flexed and extended positions. Illustratively, the prosthesis 10 is capable of a flexion angle of approximately 145 degrees. As noted above, the bearing component 16 of the knee prosthesis 10 operates to transfer many or all of the applied loads from the femoral component 12 to the tibial tray 18. As such, of the hinge assembly 14 mainly operates to stabilize the knee prosthesis 10 and guide the motion of the knee prosthesis 10 through flexed and extended positions. Of course, the hinge assembly 14 may operate to transfer some load across the components as well. By providing a variable axis of rotation as the hinge pin 100 translates through the slots 20, the weight loads carried across the bearing component 16 may be evenly distributed throughout the entire range of motion.

Figure 3:
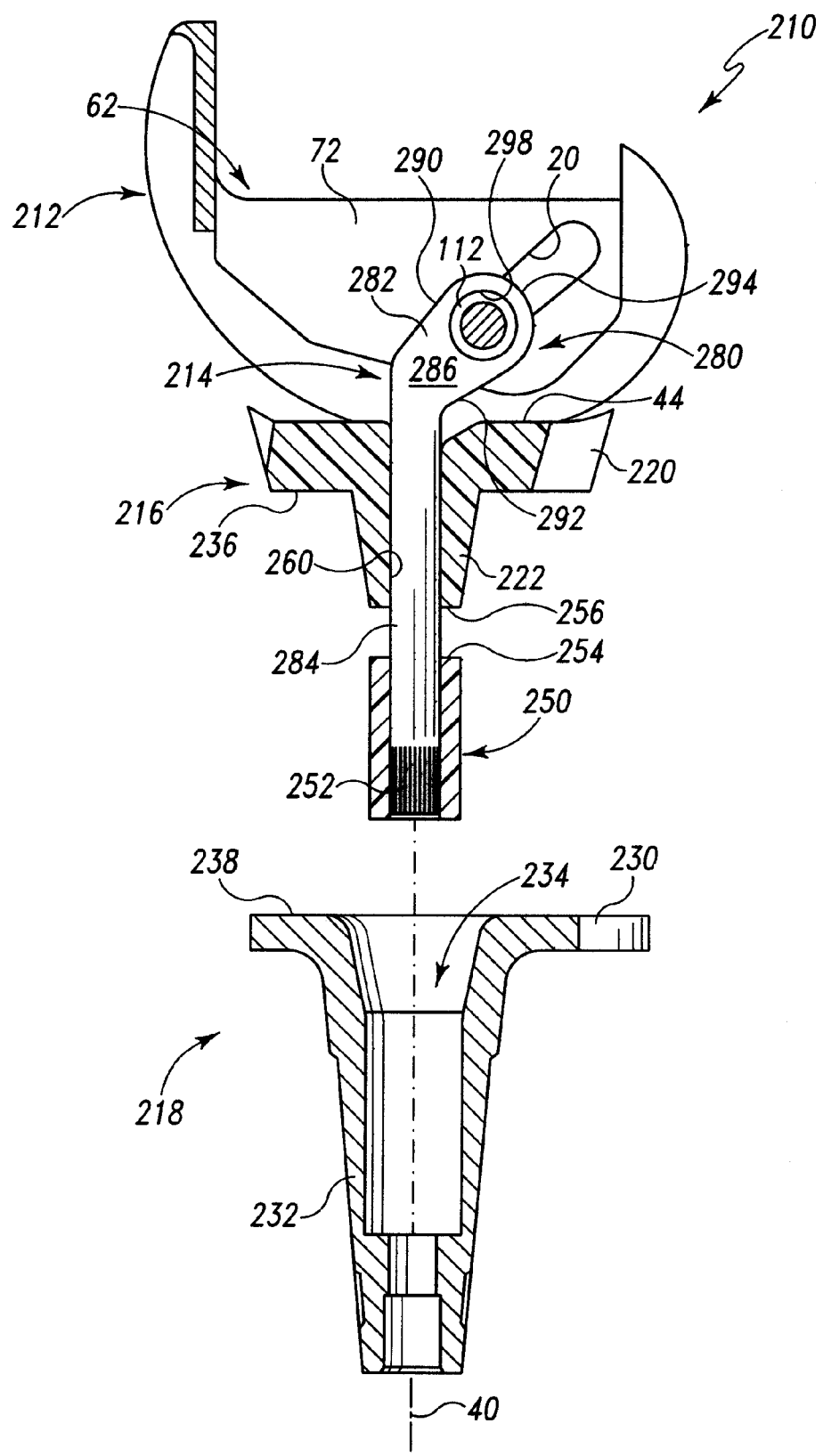
FIG. 3 is a part-sectional side view of another hinged knee prosthesis.

Looking now to FIG. 3, an alternative hinged knee prosthesis 210 is provided. Similar to the hinged knee prosthesis 10 shown in FIGS. 1 and 2, the hinged knee prosthesis 210 includes a femoral component 212, a bearing component 216, a tibial tray component 218 and a hinge assembly 214. The femoral component 212 of the prosthesis 210 is similar to the femoral component 12 of the prosthesis 10. As such, like reference numerals have been used to denote like components. In particular, the femoral component 212 includes the elongated slots 20 formed within the side walls 70, 72 of the femoral component 212.

The bearing component 216 of the prosthesis 210 includes a platform 220 and a stem 222 coupled to a bottom surface 236 of the platform 220 and configured to extend downwardly therefrom. An upper surface of the platform 220 illustratively defines the bearing surfaces 42, 44 of the bearing component 216. A generally cylindrical bore 260 is formed through the platform 220 and the stem 222 of the bearing component 216 and receives a portion of the hinge assembly 214 therethrough as is discussed in greater detail below.

The tibia tray 218 of the prosthesis 210 includes a platform 230 from which a stem 232 extends. The tibial stem 232 is configured to be implanted into a prepared end of a patient's tibia (not shown). The a generally flat bottom surface 236 of the illustrative bearing component 216 is configured to rest upon the generally flat top surface 238 of the platform 230. The stem 222 of the bearing component 216 is received within an elongated cylindrical cavity 234 formed in the tibial tray 218. The bearing component 216 is rotatable relative to the tibial tray 218 about the axis 40 running through the cavity 234 of the tibial tray 218.

Similar to the hinge assembly 14 discussed above, the hinge assembly 214 of the prosthesis 210 is pivotably coupled to the femoral component 212 and is received through the bearing component 216 and within the tibial tray 218 in order to stabilize relative movement between the femoral component 212 and the bearing component 216. Further, as noted above, the femoral component 212 of the illustrative prosthesis 210 includes guide slots 20 to guide and limit the range of motion of the femoral component 212 of the prosthesis 210 while also providing a variable axis of rotation through the hinge pin 100 of the hinge assembly 214. Similarly, this variable axis of rotation permits the femoral component 212 to slide and rotate on the bearing component 216 which aides in evenly transferring weight loads from the femoral component 212 across the bearing component 216 and to the tibial tray 218 as the prosthesis moves between flexed and extended positions.

The hinge assembly 214 includes a metal piston 280 having a head 282 and a shaft 284 coupled to the head 282. Illustratively, the head 282 includes two side walls 286, an angled top wall 290, an angled bottom wall 292 connected to the angled top wall 290 at a posterior curved portion 294. Illustratively, a bore 298 extending in a medical/lateral direction is formed through the head 282 of the piston 280 to extend between the side walls 286. The shaft 284 generally defines a circular cylinder and is received through the cylindrical bore 260 of the bearing component 216 and into the cylindrical cavity 234 of the tibial tray 218.

The hinge assembly 114 further includes the hinge pin 100 to be received through the bore 298 formed in the head 282 of the piston 280. As shown in FIG. 3, for example, the hinge pin 100 is also received through the slots 20 formed within the side walls 70, 72 of the femoral component 212 in order to couple the piston 280 of the hinge assembly 214 to the femoral component 212, as is discussed in greater detail below. Illustratively, the hinge pin 100 of the hinge assembly 114 is the same as or similar to the hinge pin 100 of the hinge assembly 14. As such, like reference numerals have been used to denote like components. Bushings 110, 112 of the hinge assembly 214 may be coupled to the outer ends of the hinge pin 100. Further, although not shown, slot covers 114 may also be provided to snap into the slots 20 and shield the open portions of the each slot 20 from the surrounding bone.

As stated above, the stem 282 of the piston 280 of the hinge assembly 214 is received through the bore 260 of the bearing component 216 and into the elongated cylindrical cavity 234 of the tibial tray 218. The head 282 of the piston 280 is positioned within the cam box 62 and between the side walls 70, 72 of the femoral component 212 such that the bore 298 of the head 282 is aligned with the slot 20 formed in each side wall 70, 72 of the femoral component 212. The hinge pin 100 is received through the slot 20 formed in the lateral wall 70 of the femoral component 212, the bore 298 of the head 282, and the slot 20 formed in the medial wall 72 of the femoral component 212 in order to couple the piston 280 of the hinge assembly 214 with the femoral component 212.

The hinge assembly 214 further includes a liner or sleeve 250 coupled to a distal end 252 of the piston 280. In particular, the distal end 252 of the stem 284 of the piston 280 is knurled, as shown in FIG. 3, in order to maintain the liner 250 on the end 252 of the stem 284 and reduce relative movement between the piston 280 and the liner 250. Illustratively, the sleeve 250 is generally cylindrical in shape and defines a central bore formed to receive the distal end 252 of the stem 284 therein. The liner 250 and the distal end 252 of the piston 280 are received within the cylindrical cavity 234 of the tibial tray 218.

Similar to the piston 80 of the prosthesis 10, the piston 280 is metal and moves upwardly and downwardly within the both the cylindrical bore 260 of the bearing component 216 and the cylindrical cavity 234 of the tibial tray 218. The illustrative liner 250 is made from a polymer, such as UHMWPE, for example, and therefore operates to prevent metal-on-metal wear between the stem 284 of the piston 280 and the metal tray 218. As noted above, the liner 250 is coupled to the distal end 252 of the stem 284 of the piston 280. As such, the liner 250 moves upwardly and downwardly with the piston 280 as the prosthesis 210 is moved between flexed and extended positions, as is discussed above in regards to the prosthesis 10. In other words, the liner 250 is coupled to the stem 284 of the piston 280 to move with the piston 280 relative to both the tibial tray 218 and the bearing component 216.

As such, the liner 250 also operates to limit the upward travel of the piston 280 in order to further constrain the prosthesis 210. For example, as the piston 280 moves upwardly during extension of the prosthesis 210, an upper surface 254 of the liner 250 may contact a lower surface 256 of the stem 222 of the bearing component 216 in order to prevent the liner 250 and the piston 280 from continuing to move upwardly relative to the tray 218 and the bearing component 216. Limiting the upward movement of the piston 280 further constrains or limits the amount of extension of the prosthesis 210. Illustratively, liner 250 as well as the stem 222 of the bearing component 216 may be sized to increase or decrease amount of upwardly and downwardly travel of the piston 280. Further, the position of the liner 250 on the stem 222 may also be changed in order to adjust the amount of travel of the piston 280.

Figure 4:
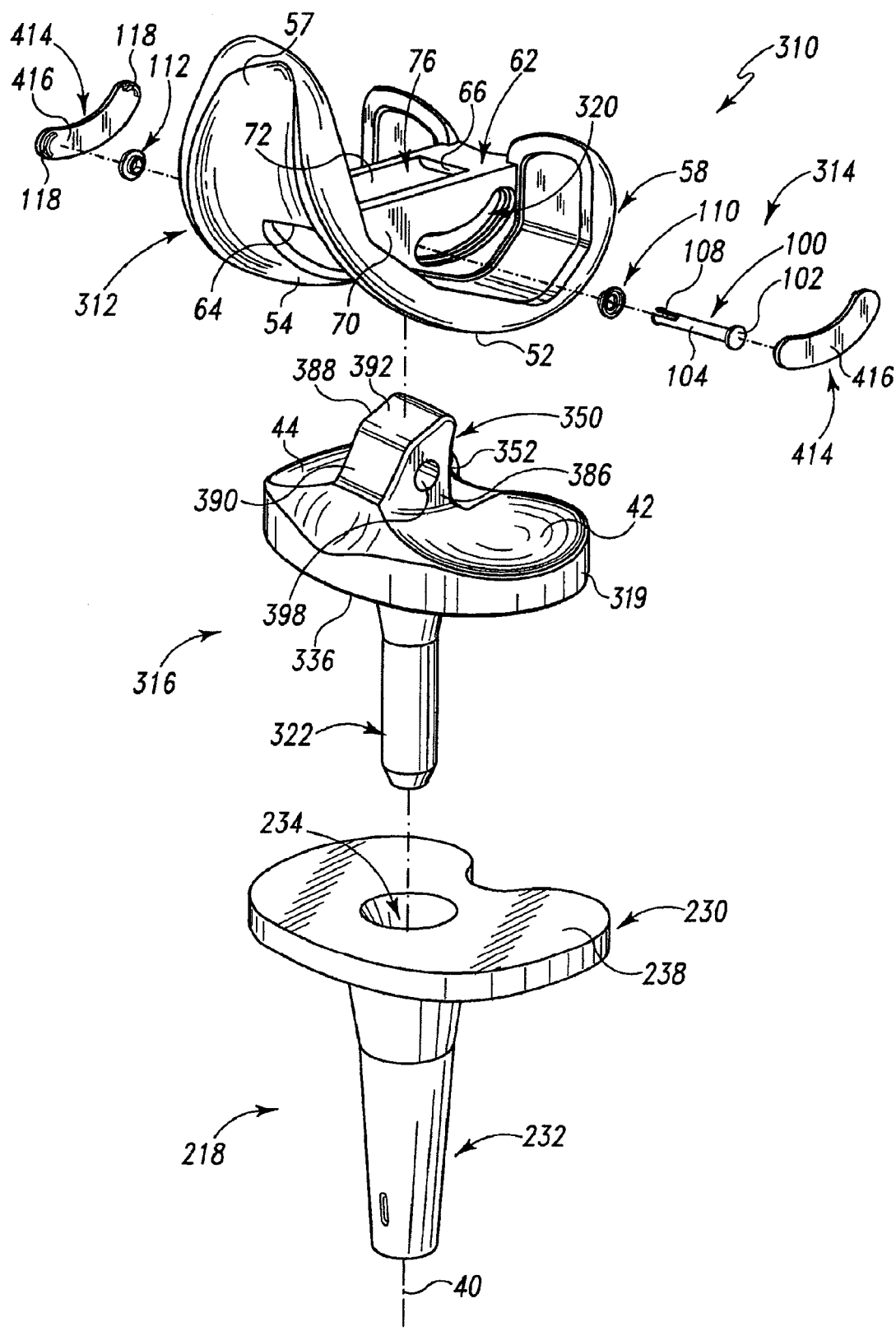
FIG. 4 is an exploded, perspective view of yet another hinged knee prosthesis.
Figure 5:
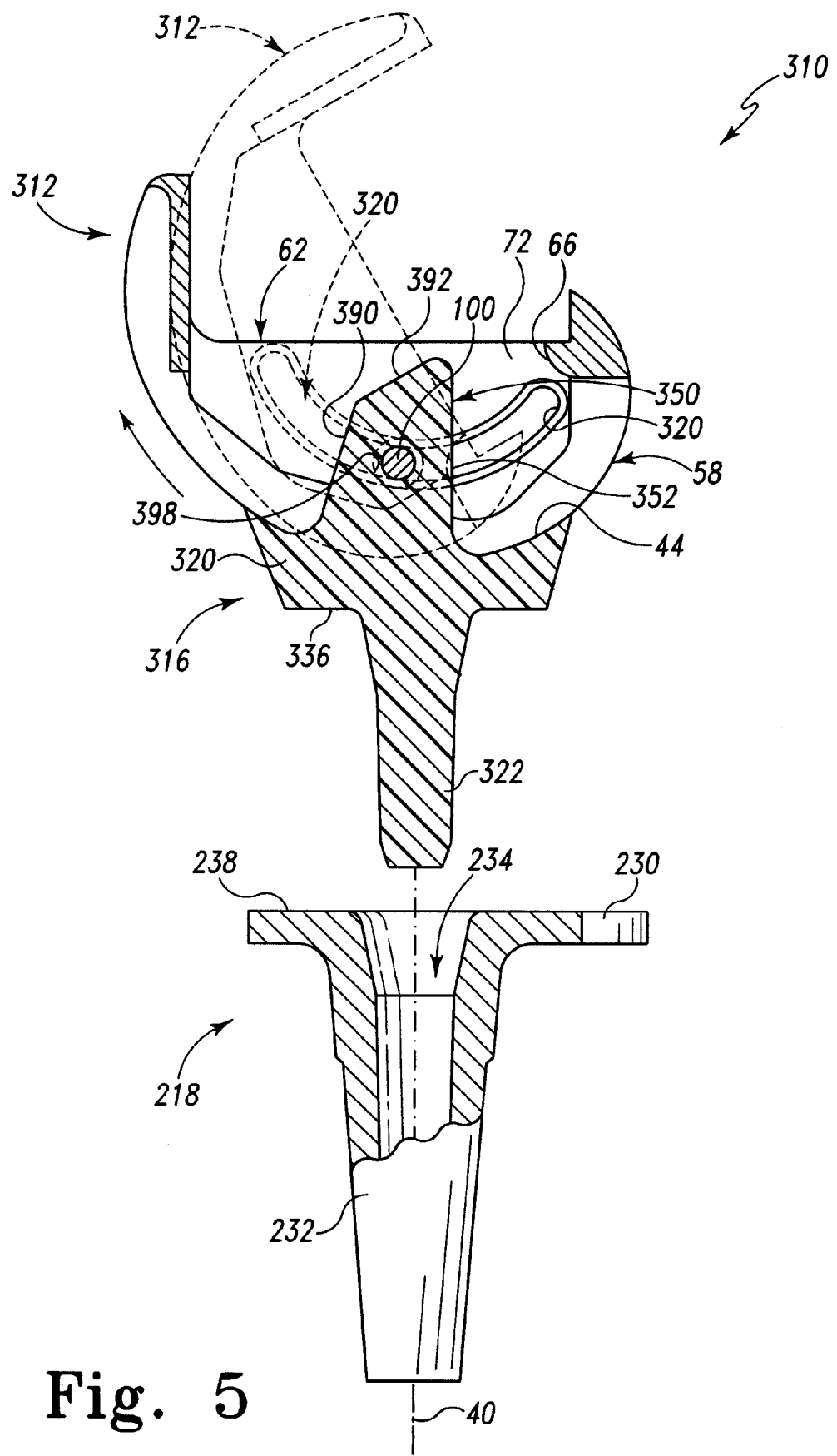
FIG. 5 is a part-sectional side view of the hinged prosthesis of FIG. 4.

Looking now to FIGS. 4 and 5, another knee prosthesis 310 is provided. The knee prosthesis 310 includes a femoral component 312, a bearing component 316, a tibial tray 218, and a hinge assembly 314. The femoral component 312 is similar to the femoral components 12, 212 described above. As such, like reference numerals are used to denote like features.

The bearing component 316 of the prosthesis 310 is a varus-valgus constrained (VCC) mobile bearing component which provides posterior stabilization to the knee prosthesis 310 in order to reduce the possibility of anterior subluxation or dislocation of the femur. In the natural knee, the posterior stability of the knee or resistance to posterior movement of the tibia with respect to the femur is provided by the posterior cruciate ligament. In cases where the posterior cruciate ligament is deficient and is no longer viable, the use of a posterior stabilized knee prosthesis, such as the prosthesis 310, may be used. Typically, the bearing component of a posterior stabilized knee prosthesis includes a spine, such as the spine 350 between the articular condyles 42, 44 of the bearing component 316. During flexion of the prosthesis 310, the posterior surface of the spine interacts with a cam on the posterior aspect of the femoral component 312 to provide posterior stability to the prosthesis 310.

In cases where the patient has collateral ligament deficiency, a varus/valgus constrained (VVC) implant may be used. Again, the varus/valgus constraint operates to prevent or resist liftoff. As such, the varus/valgus constraint is provided by raising and reinforcing the tibial spine 350 and by using a tighter fit between the side walls of the tibial 350 spine and the corresponding side walls 70, 72 of the femoral cam box 62. The width of the cam box 62 compared to the width of the spine 350 may be carefully selected to allow only a small degree of condylar liftoff, thus providing varus/valgus stability to the knee without inducing excessive forces to the spine and to the bone/implant fixation interfaces.

Looking now to FIGS. 4 and 5, the bearing component 316 includes a platform 319 defining the lateral bearing surface 42 and the medial bearing surface 44. The bearing component 316 further includes a stem 322 coupled to a bottom surface 336 of the platform 319 of the bearing component 316 and positioned to extend downwardly therefrom. The illustrative stem 322 is generally conical in shape and is formed to be received within the elongated cylindrical cavity 234 of the tibial tray component 218 such that the bottom surface 336 of the platform 319 of the bearing component 316 is adjacent to and engaged with the top surface of the platform 230 of the tray 218.

The bearing component 316 further includes the spine 350 coupled to the platform 319 of the bearing component 316 and positioned to extend upwardly therefrom. In particular, the spine 350 is positioned between the lateral and medial condyle surfaces 42, 44 of the bearing component 316. The spine 350 includes a generally vertical posterior surface 352, medial and lateral surfaces 386, 388, an angled anterior surface 390, and an angled superior or top surface 392. The posterior surface 352 of the spine operates as a cam follower against a cam surface 66 of the femoral component 312, described in greater detail below. Illustratively, the spine 350 includes a bore 398 extending between the medial and lateral surfaces 386, 388 of the spine 350. As such, the bore 398 extends in a medical/lateral direction through the spine 350. As is discussed in greater detail below, the hinge assembly 314 of the prosthesis 310 operates to mechanically couple or link the spine 350 of the bearing component 316 with the femoral component 312.

The femoral component 312 of the knee prosthesis 310 is similar to the femoral components 12, 212 described above. As such, like reference numerals are used to denote like components and features. Additionally, the cam box 62 of the femoral component 312 includes an anterior cam face 64 and a posterior cam face 66 which interacts with corresponding cam surfaces of the spine 350 as the prosthesis 310 moves between flexed and extended positions. For example, the posterior surface 352 of the spine 350 may interact with the posterior cam surface 66 of the cam box 62 when the prosthesis 310 is in the flexed position. Similarly, surfaces 390, 392 of the spine 350 may interact with the anterior cam surface 64 when the prosthesis 310 in an extended position.

Further, the femoral component 312 of the knee prosthesis 310 includes elongated, curved slots 320 formed in each side wall 70, 72 of the cam box 62 of the femoral component 312. In other words, while the slots 20 of the femoral components 12, 212 are generally straight, the slots 320 of the femoral component 312 of the knee prosthesis 310 are curved, as shown in FIGS. 4 and 5.

Generally, the curved shape of the slots 320 follows the curved outer condylar surface of the respective condyles 52, 54 of the femoral component 312. For example, as discussed above and shown in FIG. 9, each condylar member 58 defines an outer, curved surface 52, 54 which each includes curved segments S1, S2, and S3 each having a radii R1, R2, and R3 respectively. The segments S1, S2, and S3 form a smooth surface such that the radii R1, R2, and R3 at the interface between the adjacent surface segments S1, S2, and S3 have common tangents. Illustratively, the curvature of each slot 320 of the femoral component 312 follows the curvature of the condylar members 58 such that each slot 320 similarly includes curved segments each having a radii which corresponds to the radii R1, R2, R3 of the condylar members 58. In other words, the curvature of each slot 320 formed in the cam box 62 of the femoral component 312 follows the curvature of the condylar members 58.

The hinge assembly 314 of the knee prosthesis 310 includes the hinge pin 100, bushings 110, 112 and slot covers 414 discussed above in regards to the hinge assemblies 14 and 214. Illustratively, the slot covers 414 include a curved body 416 corresponding to the curved shape of the slots 320. The hinge assembly 314 of the prosthesis 310 does not include a piston component such as the pistons 80 and 280 described above. However, the hinge assembly 314 of the prosthesis 310 operates to mechanically link the femoral component 312 with the bearing component 316 in order to constrain the movement of the femoral component 312 relative to the bearing component 316. Further, the curved slots 320 of the femoral component 312 operate to guide the movement of the femoral component 312 relative to the bearing component 316 to provide a variable axis of rotation of the femoral component to allow the weight of the femur to be evenly distributed throughout the range of motion of the knee prosthesis 310.

In use, the tibial tray component 218 is secured to a prepared tibia (not shown) of a patient and the bearing component 316 is received within the elongated conical bore 34 of the tibial tray component 218. In particular, the cone or stem 322 of the bearing component 316 is received within the elongated conical bore 234 of the tibial tray component 218 such that the bottom surface 336 of the platform 319 of the bearing component 316 is adjacent to and engages the top surface 38 of the platform 230 of the tibial tray component 218. Illustratively, the bearing component 316 operates as a rotational platform of the knee prosthesis 310 such that the bearing component 316 is able to rotate about the axis 40 extending through the stem 232 of the tibial tray component 218 relative to the tibial tray component 218. In other words, the rotational motion of the illustrative bearing component 316 relative to the tray component 218 is generally not hindered or restricted. It is, of course, within the scope of this disclosure, however, to restrict the rotational motion of the bearing component relative to the tibial tray component 218 and/or to provide a fixed bearing component which is generally not able to rotate relative to the tibial tray component. Similarly, rotationally fixed or restricted bearing components may be provided for any of the knee prostheses disclosed herein.

The spine 350 of the bearing component 316 is received within the cam box 62 of the femoral component 312 such that the medial side 386 of the spine 350 is adjacent the medial side wall 70 of the cam box 62 and the lateral side 388 of the spine 350 is adjacent the lateral side wall 72 of the cam box 62. The hinge pin 100 of the hinge assembly 314 is received through the side walls 70, 72 of the cam box 62 and the bore 398 of the spine 350 in order to pivotably couple the bearing component 316 and the femoral component 312 to one another. Specifically, the hinge pin 100 is received through the elongated, curved slot 320 formed in each side wall 70, 72 of the cam box 62 and is able to translate along the slots 320 in a path defined by the curvature of the slots 320. As noted above, the curvature of the slots 320 is the same as or similar to the curvature of the condylar members 58 of the femoral component 312. As such, movement of the femoral component 312 relative to the bearing component 316 is restricted to the motion defined by the slots 320.

In use, therefore, as the knee prosthesis 310 moves between flexed and extended positions, the movement of the femoral component 312 relative to the bearing component 316 is limited at least in part by the shape and size of the slots 320. In other words, the hinge pin 100 coupling the femoral component 312 to the bearing component 316 effectively restrains the motion of the femoral component 312 to the size and shape of the slots 320. While the illustrative slots 320 are shown to have a particular length, width, and curvature relative to the other features of the femoral component 312, it is within the scope of this disclosure to provide a slot having any suitable length, width, and curvature.

For some surgical applications, certain components of the knee prosthesis 310 may be used as a typical varus/valgus constrained knee prosthesis without the need to hinge the femoral component 312 to the bearing component 316. In other words, the knee prosthesis 310 is able to convert from a VCC knee prosthesis to a hinged, VCC knee prosthesis. For example, an initial or first total knee replacement surgery may use the tray component 218 and slotted femoral component 312 shown in FIGS. 4 and 5 while implementing either the bearing component 316 or another bearing component (not shown) similar in structure to the bearing component 316 but without the bore 398 formed through the spine 350 of the bearing component 316. In either case, the surgeon may choose to not utilize the hinge assembly 314 to link the femoral component 312 and the bearing component 316 together. Such a knee prosthesis may remain in place within the patient until the knee prosthesis becomes unstable.

At this point, the surgeon may perform a revision knee replacement surgery in order to improve the stability of the knee prosthesis by adding additional constraints. One such additional constraint may be the hinge assembly 314, for example. As such, rather than replacing all components of the previously-implanted knee prosthesis, the surgeon may simply remove the alternative bearing component for use with the non-hinged knee prosthesis and replace it with another bearing component for use with a hinged knee prosthesis, such as the bearing component 316, which is suitable to receive a hinge assembly, such as the hinge assembly 314, for example. Once the bearing component has been replaced, the surgeon may install the hinge assembly 314 in order to couple the bearing component 316 with the femoral component 312 to link the two components 312, 316 together and further constrain the motion of the femoral component 312 to that defined by the slots 320 of the femoral component 312. Of course, in situations where the bearing component 316 is already implanted into the patient, the surgeon may simply add the hinge assembly 114 to the components to further constrain the relative motion of the components.

Figure 6:
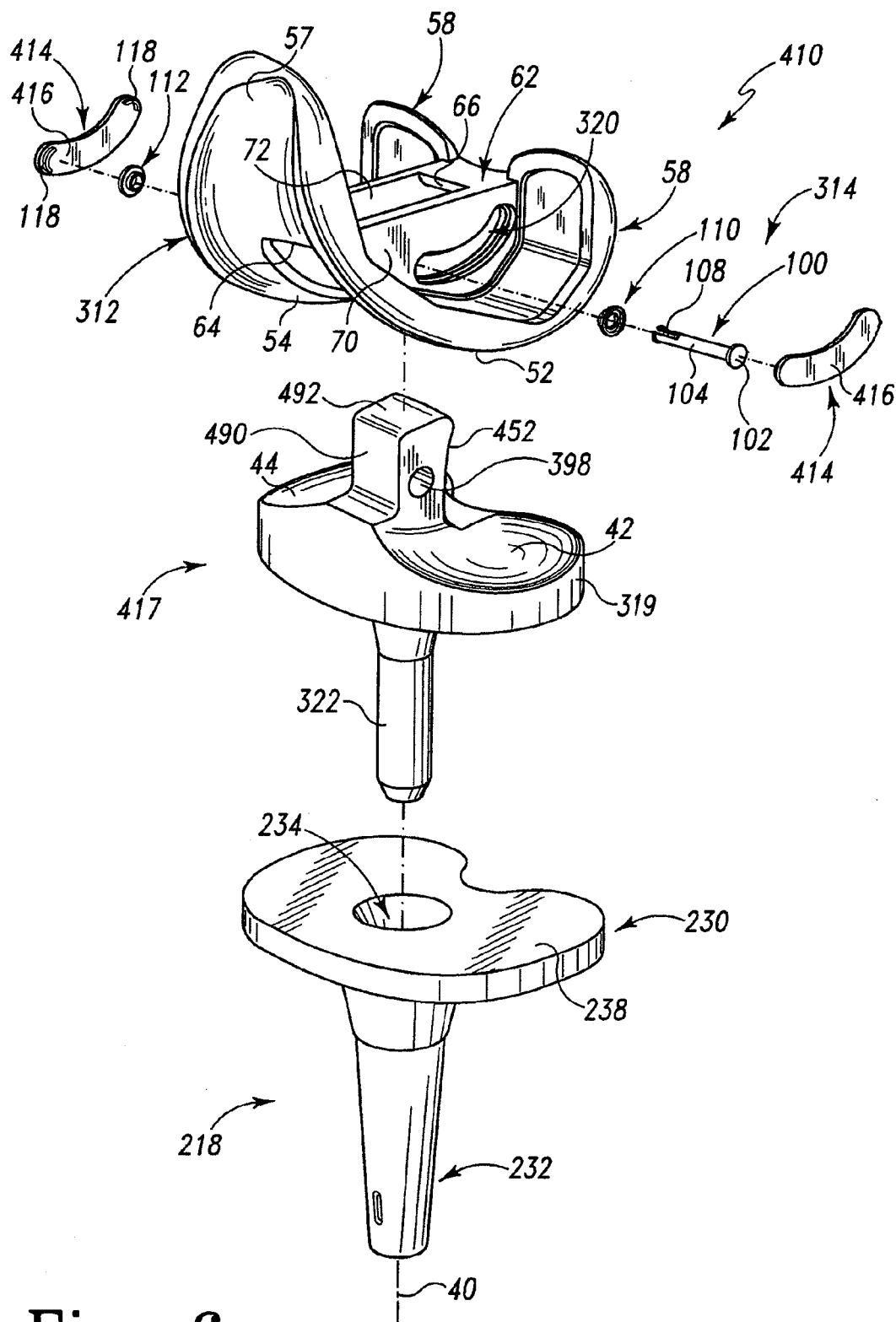
FIG. 6 is an exploded, perspective view of another hinged knee prosthesis.

Looking now to FIG. 6, another knee prosthesis 410 is provided. Similar to the knee prosthesis 310 shown in FIGS. 4 and 5, the knee prosthesis 410 is a VVC knee prosthesis including the hinge assembly 314. As such, like reference numerals have been used to denote like components. The knee prosthesis 410 includes a bearing component 417 having a spine 450 shaped differently than the spine 350 disclosed above with respect to the knee prosthesis 310. For example, the spine 450 of the bearing component 417 includes a generally vertical anterior surface 490 and a top or superior surface 492 which is angled from horizontal to a lesser degree than the top surface 392 of the spine 350. The generally vertical anterior surface 452 of the spine 450 generally operates to further prevent over-extension of the femoral component 312 relative to the bearing component 417. The spine 450, however, also includes the bore 398 formed therethrough and the hinge pin 100 of the hinge assembly 314 is received through the bore 398 and the slots 320 of the femoral component 312 in order to couple the femoral and bearing components 312, 417 together. The operation of the knee prosthesis 410 is similar to, if not the same as, the operation of the knee prosthesis 310 in that the motion of the femoral component 312 is limited to the size and shape of the slots 320 formed in the stabilizing box 62 of the femoral component 312.

Figure 7:
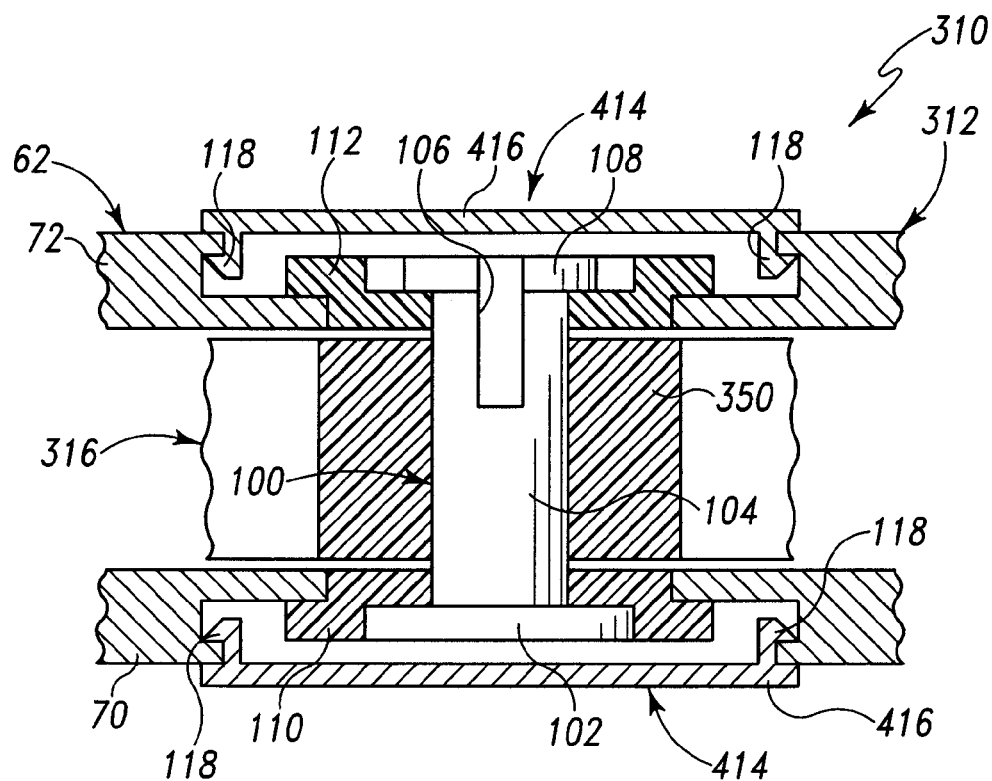
FIG. 7 is a top sectional view of the hinged knee prosthesis of FIGS. 4 and 5 including a hinge pin assembly coupling a femoral component and a bearing component of the hinged knee prosthesis together.

Looking now to FIG. 7, a part-sectional, part-fragmentary view of the knee prosthesis 310 of FIGS. 4 and 5 is provided. Illustratively, as discussed above, the hinge pin 100 of the hinge assembly 314 is received through the bore 398 formed in the spine 350 of the bearing component 316 as well as the slots 320 formed in the side walls 70, 72 of the cam box 62 of the femoral component 312. Further as discussed above, the hinge pin 100 includes the cap 102, the body 104, and the foot 108. Further, the slot 106 is formed in the body 104 of the pin 100 in order to allow the foot end of the pin 100 to be compressed or pinched together. Further, as noted above, both the hinge pin 100 and the femoral components 312 are made from metal. As such, plastic or polymer bearings 110, 112 are coupled to the respective cap 102 and foot 108 of the pin 100 and are received within the slots 320 of the femoral component 320 to prevent metal-on-metal wear between the pin 100 and the slots 320. Illustratively, therefore, the bearings 110, 112 carry the hinge pin 100 and translate within the slots 320 as the femoral component 312 moves relative to the bearing component 316.

As further discussed above, the knee prosthesis 310 (as well as the knee prostheses 10, 210, and 410) includes slot covers 414 which are coupled to the femoral component 312 in order to cover the slots 320. The slot covers 414 operate to cover the slots 320 in order to prevent or reduce any bone ingrowth of the patient's natural femur into the open slots 320. The illustrative slot covers 414 include a curved body 416 and flexible flanges 118 which may be snapped into the slots 320, as shown in FIG. 7. Illustratively, the slot covers 414 provided to cover the elongated, curved slots 320 of the femoral component 312 are similarly curved while the slot covers 114 provided to cover the elongated, generally straight slots 20 of the femoral components 12 and 212 are similarly straight. In other words, the shape of the slot covers of each prosthesis correspond to the shape of the slots formed in the femoral component of each prosthesis.

Figure 8:
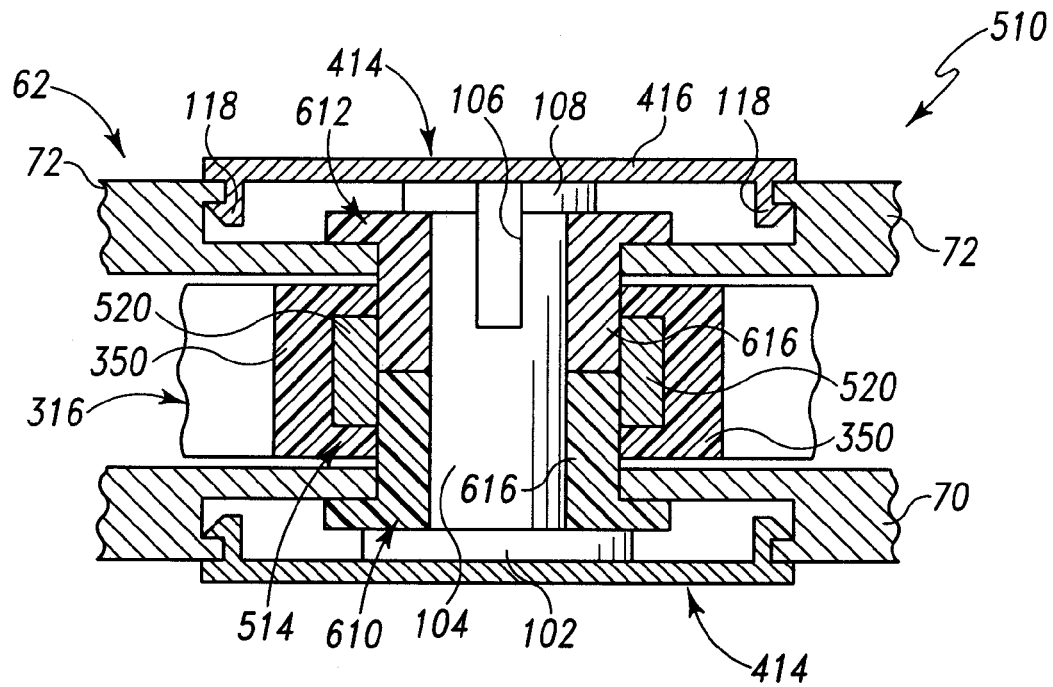
FIG. 8 is a top sectional view of another hinged knee prosthesis including an alternative hinge pin assembly.

Looking now to FIG. 8, a part-sectional, part-fragmentary view of another knee prosthesis 510 is provided. Illustratively, the knee prosthesis 510 is similar to the knee prosthesis 310; as such, like reference numerals have been used to denote like components. A hinge assembly 514 of the knee prosthesis 510 includes polymer bearings 610, 612 similar to the polymer bearings 110, 112 shown in FIG. 7. However, the polymer bearings 610, 612 each include sleeve portions 616 such that the body 104 of the pin 100 is received within and surrounded by the sleeve portions 616 of the bearings 610, 612. Because both the bearings 610, 612 as well as the bearing component 316 are made from a polymer, a metal bushing 520 of the hinge assembly 514 is provided between the bearing component 316 and the bearings 610, 612 in order to prevent wear between the femoral component 312 and the hinge assembly 514. Further, such bushings and bearings may prevent or reduce the components from locking up and allow the hinge pin 100, the bearing component 316, and the femoral component 312 to move smoothly and easily relative to one another. Of course, either the hinge assembly 114 shown in FIG. 7 or the hinge assembly 514 shown in FIG. 8 may be used with any of the knee prostheses disclosed herein.

While knee prostheses 10, 210, 310, 410 and 510 have been disclosed herein, it should be appreciated that the various features of each prosthesis may be incorporated into any orthopaedic prosthetic joint assembly for replacing hips, shoulders, elbows, etc. In particular, the hinge assemblies and slotted feature of the femoral components disclosed herein may be incorporated into any suitable orthopaedic joint prosthesis. For example, a hinged prosthetic joint for accommodating articulation between a first bone and a second bone may include a first component configured to be attached to the first bone and a second component configured to be attached to the second bone. The first component may include a body and an elongated slot formed in the body. A bearing component of the prosthetic joint is positioned between the first and second components and a hinge assembly, such as the hinge assemblies 14, 114, 214, 314 described above, may include a hinge pin received within the slot of the first component.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A hinged knee prosthesis comprising:
a femoral component configured to be coupled to a femur and including a body and a side wall having an elongated slot formed therein,
a tibial component configured to be coupled to a tibia and defining a cavity,
a polymer bearing component positioned between the femoral component and the tibial component, the bearing component having (i) a medial bearing surface configured to articulate with a medial condyle surface of the femoral component and (ii) a lateral bearing surface configured to articulate with a lateral condyle surface of the femoral component, and
a hinge assembly to pivotably couple the femoral component to the tibial component and to substantially prevent anterior/posterior movement of the bearing component with respect to the tibial component, the hinge assembly including (i) a piston configured to be received within the cavity of the tibial component and (ii) a hinge pin received through a bore formed in the piston and the elongated slot of the femoral component, the hinge pin to translate along the elongated slot relative to the femoral component to provide a variable axis of rotation for the femoral component.

2. The hinged knee prosthesis of claim 1, wherein
the bearing component includes an aperture and the piston is received through the aperture of the bearing component, and the piston of the hinge assembly interfaces with the aperture of the bearing component and cavity of the tibial component to prevent substantial anterior/posterior movement of the bearing component with respect to the tibial component.

3. The hinged knee prosthesis of claim 1, wherein:
the femoral component includes a second side wall spaced-apart from the side wall, the second side wall including a second elongated slot, and
the hinge pin is received through the second elongated slot.

4. The hinged knee prosthesis of claim 3, wherein:
the piston includes a head and a shaft coupled to the head such that the bore of the piston is formed through the head of the piston, and
the head of the piston is positioned between the side walls of the femoral component.

5. The hinged knee prosthesis of claim 1, wherein the hinge pin is made from metal, the femoral component is made from metal, and the piston is made from metal.

6. The hinged knee prosthesis of claim 5, wherein the hinge assembly further includes a polymer bearing coupled to the pin and positioned between the pin and the portion of the femoral component defining the slot.

7. The hinged knee prosthesis of claim 1, wherein the hinge assembly further includes a slot cover configured to be coupled to the femoral component in order to cover the elongated slot.

8. The hinged knee prosthesis of claim 1, wherein the elongated slot is generally straight.

9. The hinged knee prosthesis of claim 1, wherein the elongated slot includes an anterior end and a posterior end positioned superiorly from the anterior end.

10. A hinged knee prosthesis comprising:
a femoral component configured to be coupled to a femur and including a side wall having an elongated slot formed therein,
a tibial component configured to be coupled to a tibia,
a polymer bearing component positioned between the femoral component and the tibial component, the bearing component having (i) a medial bearing surface configured to articulate with a medial condyle surface of the femoral component and (ii) a lateral bearing surface configured to articulate with a lateral condyle surface of the femoral component, and
a hinge assembly to pivotably couple the femoral component to the tibial component, the hinge assembly including a hinge pin received through the elongated slot of the femoral component, the hinge pin to translate along the elongated slot as the femoral component and tibial component move between an extended position and a flexed position, wherein
the bearing component is coupled to the tibial component such that flexion of the hinged knee prosthesis between the extended position and the flexed position to substantially prevent anterior/posterior movement of the bearing component with respect to the tibial component.

11. The hinged knee prosthesis of claim 10, wherein the elongated slot is curved.

12. The hinged knee prosthesis of claim 11, wherein a curvature of the elongated slot is the same as a curvature of a condylar member of the femoral component.

13. The hinged knee prosthesis of claim 10, wherein the elongated slot is straight.

14. The hinged knee prosthesis of claim 10, wherein the hinge assembly further includes a piston having a bore formed therein and the hinge pin is received through the bore.

15. The hinged knee prosthesis of claim 14, wherein
the piston includes a head having the bore formed therein and a stem coupled to the head and received within an elongated cavity of the tibial component,
the bearing component includes an aperture formed therethrough and the piston is received through the aperture, and
the piston interfaces with the aperture of the bearing component and the elongated cavity of the tibial component to substantially prevent anterior/posterior movement of the bearing component with respect to the tibial component.

16. The hinged knee prosthesis of claim 14, wherein
the bearing component includes an aperture formed therethrough and a stem received within an elongated cavity of the tibial component,
the piston is received through the aperture of the bearing component, and
the stem of the bearing component interfaces with the elongated cavity of the tibial component to substantially prevent anterior/posterior movement of the bearing component with respect to the tibial component.

17. The hinged knee prosthesis of claim 10, wherein the bearing component includes a spine positioned between a medial bearing surface and a lateral bearing surface of the bearing.

18. The hinged knee prosthesis of claim 17, wherein the spine of the bearing component includes a bore formed therethrough and the hinge pin of the hinge assembly is received through the bore.

19. The hinged knee prosthesis of claim 17, wherein the femoral component includes a second side wall having a second elongated slot, and wherein the spine of the bearing component is positioned between the side walls of the femoral component.

20. A hinged knee prosthesis of claim 10, wherein the femoral component and the bearing component are configured to rotate together relative to the tibial component about an axis through a stem of the tibial component.

21. A hinged prosthetic joint for accommodating articulation between a first bone and a second bone, the joint comprising:
a first component configured to be attached to the first bone, the first component having a body comprising a side wall and an elongated slot formed in the side wall of the body,
a second component configured to be attached to the second bone,
a polymer bearing component positioned between the first component and the second component, the bearing component having (i) a medial bearing surface configured to articulate with a medial condyle surface of the femoral component and (ii) a lateral bearing surface configured to articulate with a lateral condyle surface of the femoral component, and
a hinge assembly including a hinge pin received within the slot of the first component, the hinge pin to provide a variable axis of rotation for the first component as the joint is moved between extended position and a flexed position, wherein
anterior/posterior movement of the bearing component is inhibited substantially as the hinged prosthetic joint is flexed between an extended position and a flexed position.

* * * * *